United States Patent
Kerr et al.

(10) Patent No.: US 7,202,838 B2
(45) Date of Patent: Apr. 10, 2007

(54) VIEWING DEVICE

(75) Inventors: Roger S. Kerr, Brockport, NY (US);
Timothy J. Tredwell, Fairport, NY (US); Badhri Narayan, Rochester, NY (US); Sujatha Ramanujan, Pittsford, NY (US); Eric J. Donaldson, St. Paul, MN (US); Sarat K. Mohapatra, Woodbury, MN (US)

(73) Assignee: Eastman Kodak Company, Rochester, NY (US)

( * ) Notice: Subject to any disclaimer, the term of this patent is extended or adjusted under 35 U.S.C. 154(b) by 451 days.

(21) Appl. No.: 10/717,376

(22) Filed: Nov. 19, 2003

(65) Prior Publication Data

US 2005/0104896 A1    May 19, 2005

(51) Int. Cl.
   *G09G 5/00* (2006.01)
(52) U.S. Cl. .......................... 345/1.2; 40/361
(58) Field of Classification Search ................ 345/1.1, 345/1.2, 1.3, 2.1, 2.2, 2.3
   See application file for complete search history.

(56) References Cited

U.S. PATENT DOCUMENTS

| | | | |
|---|---|---|---|
| 5,790,216 A | 8/1998 | Inbar et al. | |
| 6,031,516 A | 2/2000 | Leiper | |
| 6,157,373 A | 12/2000 | Rego | |
| 6,247,857 B1 * | 6/2001 | Wheeler et al. | 396/567 |
| 6,279,253 B1 | 8/2001 | Inbar et al. | |
| 6,441,827 B1 * | 8/2002 | Hori et al. | 345/629 |
| 6,462,868 B1 * | 10/2002 | Giesberg et al. | 359/443 |
| 6,550,922 B2 * | 4/2003 | Bogomolnyi | 353/122 |
| 6,595,922 B1 | 7/2003 | Henderson et al. | |
| 7,046,213 B2 * | 5/2006 | Campbell et al. | 345/2.2 |

* cited by examiner

*Primary Examiner*—Amr A. Awad
*Assistant Examiner*—Tom Sheng
(74) *Attorney, Agent, or Firm*—Roland R. Schindler, II

(57) ABSTRACT

A viewing device and method are provided for use with an image transparency having an associated tracking memory. The viewing device has a display adapted to present at least two illumination patterns, a reader device for obtaining data stored in a tracking memory of an image transparency positioned proximate to the display surface, and a control processing unit. The control processing unit is adapted to receive the obtained data and to generate more than one illumination pattern with a first of the illumination patterns formed for passing through the transparency and second of the illumination patterns formed for viewing on the display without passing through the transparency, wherein the appearance of at least one of the illumination patterns is determined based upon the data obtained from the tracking memory.

19 Claims, 7 Drawing Sheets

VIEWING DEVICE

FIELD OF THE INVENTION

This invention generally relates to display apparatus for diagnostic images and more particularly relates to a display apparatus adapted for viewing both film and digital images and controlling access to related data.

BACKGROUND OF THE INVENTION

Networked information systems such as HIS (Hospital Information Systems) provide a useful measure of effective information management for medical data for patients admitted to hospitals or receiving outpatient care. This patient information can include textual data such as manually or automatically entered information regarding the patient. Textual data can be readily stored and accessed using networked computer systems that serve a multitude of functions from billing to patient records maintenance. However, patient information can also include medical images such as Computer Tomography images, Magnetic Resonance Imaging Images, images obtained during various procedures. The wide variety of devices that are capable of obtaining patient related medical images ensures that such images are captured using different equipment, media and methods. Further, a wide variety of different exposure, processing and development techniques are used in forming hardcopy medical images. Such hardcopy medical images, therefore can have a wide range of image densities, color qualities and an media properties that are best observed under lighting conditions that complement such characteristics and properties.

Even though many types of images are obtained and stored digitally, experienced radiologists and other medical professionals often prefer to record the digital medical images in a hardcopy form. In part, this is done because despite the many advances in digital imaging technologies, many medical facilities continue to rely upon hardcopy paper files and folders as the ultimate repository of medical information for each patient. Such a hard copy repository provides an inherent level of security and reliability. However, there remains a recognized need for more efficient ways of maintaining and managing hardcopy medical images, and other medical records for associating these images and records with the complete set of patient data some portions of which may be only available in electronic form at certain points in time. It is vital for effective patient care that the correct medical images needed to diagnose and treat a patient's condition be obtained, that the images are positively identified so that there is minimal chance of confusion due to mismatched images, and that medical images be correlated with other medical records about the patient. It is also important that patient privacy be properly maintained, with checks on authorization and security that help to ensure privacy and help to obtain the proper medical care, without jeopardizing quality and timeliness.

An important tool in observing medical images is the conventional light box. This device has a display platform that projects a generally uniform light pattern in a manner that passes through X-ray and other medical images in order to facilitate observation of these images. These images, printed on film, show the appropriate detail with the sufficient backlight illumination. However, the conventional light box provides only one kind of light for viewing such films. The light does not adapt to the characteristics of the image being viewed using the light box, or the shape of the image being viewed using the light box.

However, there can be a need to view both hardcopy images in concert with digital images of and or textual data patient data, and solutions have been proposed for a hybrid light box for conventional film and for digital data and images. For example, U.S. Pat. No. 6,031,516 entitled "Integrated Film and Filmless Image Display System" to Leiper discloses a viewing workstation that allows a medical professional to access and view an X-ray image from a roll of images. Then, from a bar code on the X-ray, a link is provided to electronically stored images for the same patient. These images are then displayed on a display monitor.

Related solutions include U.S. Pat. No. 5,790,216 entitled "Viewing Apparatus and Work Station" to Inbar et al., which also discloses a backlight apparatus having an auxiliary display for electronic data. U.S. Pat. No. 6,157,373 entitled "Method and Apparatus for Displaying Images" to Rego discloses sensing a bar code or other indicia on a film image for obtaining an electronic image, including use of a touch-sensitive display surface for displayed films.

While the systems that Leiper '516, Inbar et al. '216, and Rego '373 disclose provide the capability for viewing both film and electronic data and images, there is substantial room for improvement with respect to image management, access security and log maintenance, and user interaction. For example, the Leiper '516 and Rego '373 disclosures describe sensing a bar code on a medical record and obtaining the electronic image data that corresponds to an image on film. The bar code thus provides a read-only "pointer" to the larger database. Further, these systems typically address primarily the need to present only one image to a user using the light box. However, it will be appreciated that, in practice, much useful diagnostic information can be obtained by comparing one medical image against another medical image, by examining a medical image in context with comments, information, and notes made by other professionals, and in context with other patient related information. These needs are largely unaddressed in the art.

Thus there are numerous additional opportunities for improvement of diagnosis and treatment using a viewing device as part of a larger medical imaging system and it can be seen that there is a need for a viewing solution that enables viewing of both film and digital images and other information in a user-friendly manner and cooperates with other data processing and storage systems to provide the full body of available patient data to an attending diagnostician.

SUMMARY OF THE INVENTION

In one aspect of the invention a viewing device is provided for use with an image transparency having an associated tracking memory. The viewing device has a display adapted to present at least two illumination patterns, a reader device for obtaining data stored in a tracking memory of an image transparency positioned proximate to the display, and a control processing unit. The control processing unit is adapted to receive the obtained data and cause the display to generate more than one illumination pattern with a first of the illumination patterns formed for passing through the transparency and second of the illumination patterns formed for viewing on the display without passing through the transparency, wherein the appearance of at least one of the illumination patterns is determined based upon the data obtained from the tracking memory.

In another aspect of the invention, a viewing device is provided for simultaneously displaying an image transparency and at least one electronic image. The viewing device has a display surface with an adjustable light-providing area for providing an area of backlight illumination through the image transparency and an electronic image area for display of said at least one electronic image. A transceiver obtains patient identification information from a radio frequency (RF) transponder coupled to the image transparency, said RF transponder comprising a memory with the patient identification stored therein. A control processing unit is provided with a communication link for obtaining said at least one electronic image from a patient database using the patient information and causing the electronic image to be presented.

In still another aspect of the invention, display screen is provided. The display screen has a backlighting window for providing backlight illumination through a transparency; and, a display window for displaying at least one electronic image. A radio frequency transceiver obtains data from a radio frequency transponder on the transparency and a control processing unit that adjusts the appearance of the window based upon data received by the transponder.

In a further aspect of the invention a method for simultaneously operating a display for simultaneous viewing of an image transparency and at least one electronic image is provided. In accordance with the method a tracking memory coupled to the image transparency is detected and information is read therefrom. A first illumination pattern is formed for providing a backlight source through the image transparency and a second illumination pattern is formed for presenting an electronic image, wherein at least one of the first illumination pattern and the second illumination pattern are provided based upon the information read from the tracking memory.

BRIEF DESCRIPTION OF THE DRAWINGS

While the specification concludes with claims particularly pointing out and distinctly claiming the subject matter of the present invention, it is believed that the invention will be better understood from the following description when taken in conjunction with the accompanying drawings, wherein:

DETAILED DESCRIPTION OF THE INVENTION

The present description is directed in particular to elements forming part of, or cooperating more directly with, apparatus in accordance with the invention. It is to be understood that elements not specifically shown or described may take various forms well known to those skilled in the art.

Viewing Device

Figure 1:
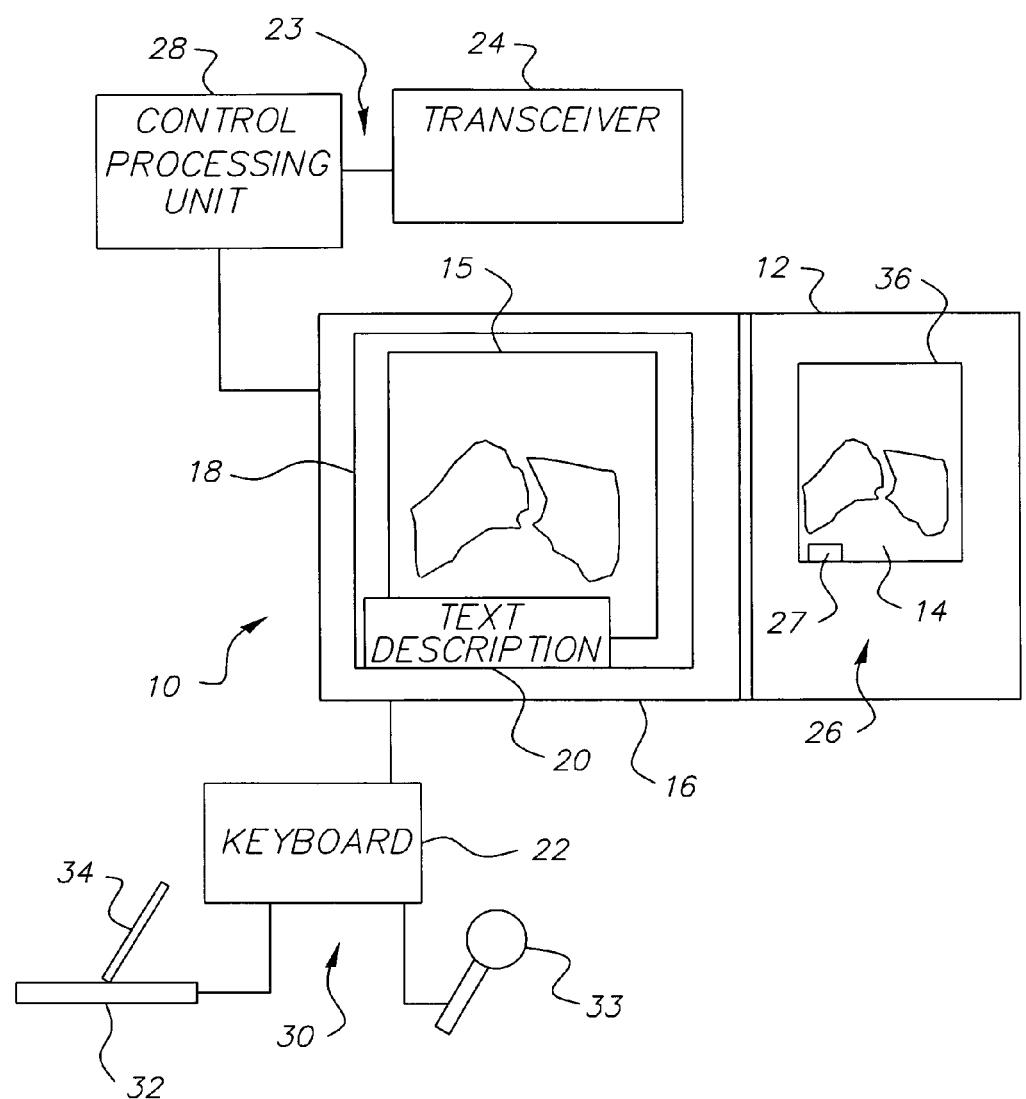
FIG. 1 is a schematic block diagram showing subsystems of a viewing device of one embodiment of the invention.

Referring to FIG. 1, there is shown one embodiment of an a viewing device 10. Viewing device 10 has a backlight portion 12 for conventional light box display of a recorded image 14 such as an image that is recorded on a film such as a transparency. An electronic display portion 16 provides a display screen 18 showing the image data obtained as image 15. Display screen 18 provides menu selections and other features for obtaining or providing information, including a text window 20 for entry or review of text data, such as from a keyboard console 22.

Viewing device 10 can provide automatic access to a database of images, and is equipped with a sensing system 23 such as RF transceiver 24 to read a tracking memory 26 such as a RF transponder 27 having information stored inside and to use the information obtained for accessing an image, or data such as on a networked database. The image or other data are obtained and an electronic image 15 is formed based upon the obtained image or data. Image 15 is presented as an illumination pattern on display screen 18 to display side by side with, or to be overlaid with, a recorded image 14. A control processing unit 28 receives signals from sensing system 23 having identifying information such as a patient identifier, or image identifier, obtained from tracking memory 26. Control processing unit 28 uses the identifying information from tracking memory 26 that can be used to obtain, for example, patient data from a referenced database.

Viewing device 10 can also provide automatic access to patient information that is stored in tracking memory 26. For example, tracking memory 26 can store information that is related to the patient and/or the medical image to which tracking memory 26 is associated. This information can include for example information indicating areas of interest in the image. This information can also include for example, an opinion offered by a medical professional who has analyzed the medical image, time date and equipment information characterizing the process by which the medical image was obtained or rendered in hard copy form.

Viewing device 10 allows a careful comparison of a digital image 15 and a recorded image 14 making it simpler to obtain images from the same angle at different times for side-by-side comparison. Viewing device 10 also makes it possible to overlay images 14 and 15 for comparison on display screen 18.

Viewing device 10 also provides a user interface system 30 for obtaining information from the medical professional. User interface system 30 can comprise any form of transducer or other device capable of receiving an input from a user and converting this input into a form that can be used by control processing unit 28 in operating viewing device 10. This can take many forms. For example, in one embodiment user interface system 30 can comprise an optional audio capture system 33, allowing storage of audio data or transcription to text, using voice recognition or transcription performed off-site. An optional tablet 32 can be provided with a stylus 34 for handwritten data entry. Backlight portion 12 or electronic display portion 16 can optionally be provided a user interface system 30 comprising, for example, a contact-sensitive surface 36 for accepting handwritten input using stylus 34, for accepting handwritten input from some other writing device or for accepting handwritten input from a touch. Thus, for example, a physician can annotate the image directly and can have this annotation stored electronically as part of the patient's medical record either by storage in the database or by storage in the tracking memory. Other forms of user interface system 30 can be used. For example, user interface system 30 can comprise a touch pad input, a 4-way switch, a 6-way switch, an 8-way switch, a trackball system, a joystick system, a voice recognition system, a gesture recognition system or other such systems.

Display Manipulation Options

Given the general arrangement of FIG. 1, there are a number of configurations available for the component of viewing device 10. For example, in one embodiment, backlight portion 12 and display screen 18 could simply be separate components with backlight portion 12 comprising a conventional backlight display comprising, for example, a light source and a light diffusion system and with display screen 18 comprising a conventional dynamic display such as Cathode Ray Tube (CRT) monitor, a Liquid Crystal Display (LCD), or an Organic Light Emitting Display (OLED) also known as an Organic Light Emitting Display (OELD). Such OLED displays are advantageous because they are emissive displays that illuminate only as necessary and do not require uniform backlighting as is required by most forms of LCD displays.

Display surface 38 can comprise single light emitting display such as OLED, a plasma display or other emissive display. In such cases there is no separate backlight, rather the entire display is pixilated and capable of grey scale. Such a display can be used as a backlight for a transparency simply by providing data to the display corresponding to the appropriate level of illumination. The display may be a black/white display or a color display. In the case of a color display, it is possible to operate in a grey scale mode by presenting color as the decomposition into the corresponding color emitters.

Figure 2A:
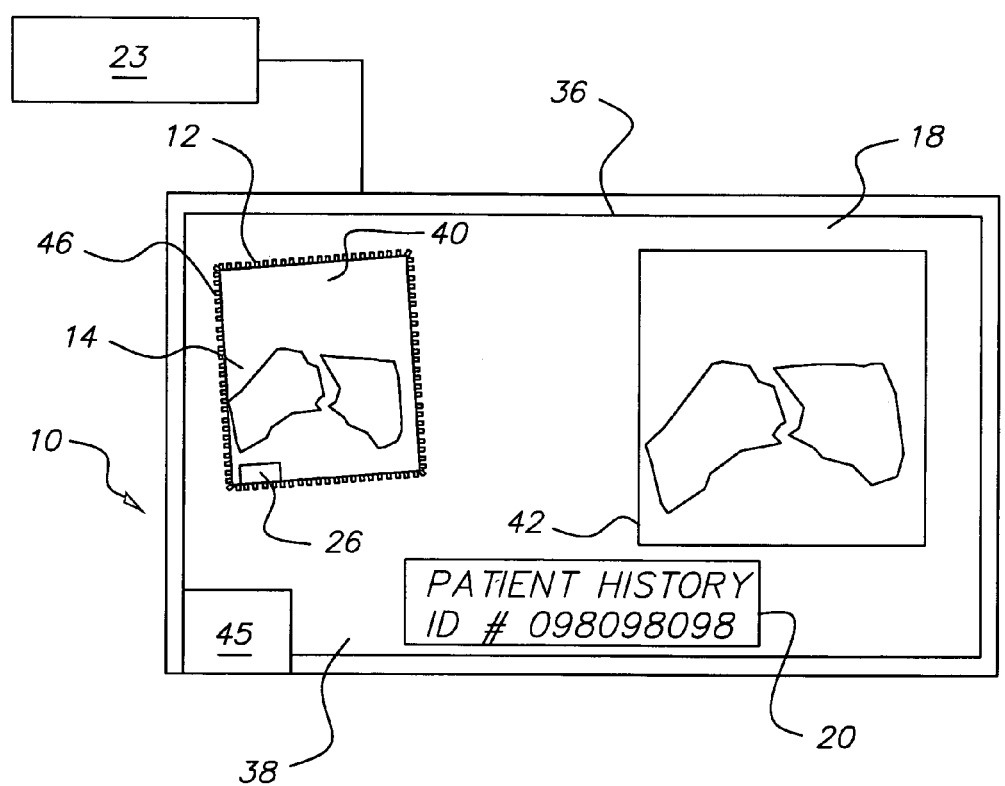
FIGS. 2a and 2b are plane views showing arrangements of film and electronic images on a viewing device according to one embodiment of the present invention.
Figure 2B:
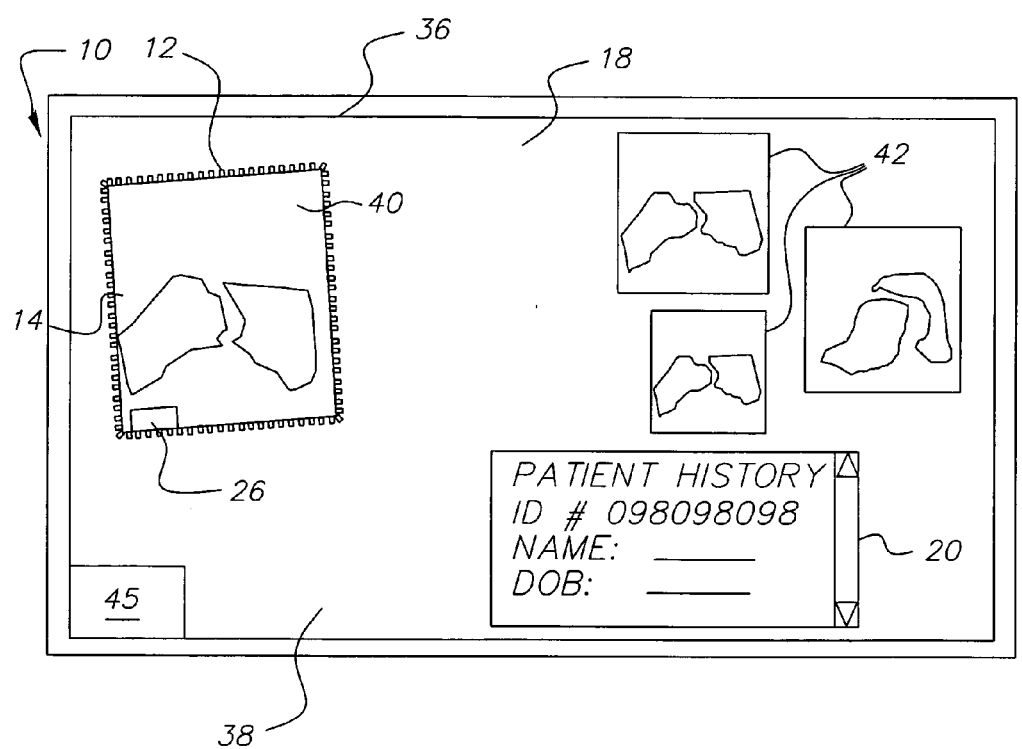

However, in another embodiment, as shown in FIGS. 2a and 2b, a single display surface 38 is used to provide, as needed, both a backlighting illumination pattern for use in projecting light through or onto a soft display and a soft display pattern that can contain, digital images, text, graphics, icons, symbols and the like. Display surface 38 may be the surface of an LCD display with appropriate backlighting. Alternatively, display surface 38 can be a tiled display, formed from an array of smaller displays, arranged contiguously to provide the effect of a single, larger display and can comprise, for example, any of a conventional Cathode Ray Tube (CRT) monitor or Liquid Crystal Display (LCD), Organic Light Emitting Display (OLED), or an Organic Light Emitting Display (OELD).

In this embodiment, when an image-bearing film 40 is placed onto display surface 38. Sensor system 23 detects the image-bearing film 40 and causes display surface 38 to provide an illumination pattern 46, corresponding to the outline of image 14, to provide backlighting only where needed. This has the advantageous effect of minimizing or eliminating glare from portions of the back lit area that do not pass through image bearing film 40. A similar masking utility for a backlighting display is disclosed in U.S. Pat. No. 6,279,253 entitled "Self-Masking Transparency Viewing Apparatus" to Inbar et al., The dimensions and location of an illumination pattern 46 can be sensed from information encoded on tracking memory 26. Alternately, display screen 18 can sense the size and position of image-bearing film 40 using for example, a positional sensor 45 such as light sensors, capacitance sensors, touch screen type sensors and conventional contact electromechanical switches, with positional sensor 45 providing a signal that indicates an area of the display surface 38 that corresponds to the position of image bearing film 40. Touch Screens may be integrated into the display screen 18, included in the encapsulation of an emissive display, or included as an overlay separate from the original display apparatus. As shown in FIGS. 2a and 2b the viewing system 10 can also detect an orientation of image bearing film 40 using positional sensor 45 and can form an illumination pattern having an orientation of image bearing film 40. This causes light box to illuminate a masked area 46 that corresponds to the size, shape and orientation of the image-bearing film 40. Where a touch screen is used, touch screen 36 can detect contact between the image bearing film 40 and the touch screen 36 and thus touch screen 36 can perform the position and orientation detection functions of positional sensor 45.

As yet another option, a viewer 48 can manually define, size, and/or orient illumination pattern 46 as a window of illumination for image-bearing film 40. This can be done using a user interface such as interface techniques for window creation and sizing. The balance of display surface 38 is then available for display of other illumination patterns such as electronic images 42, text and graphics. Optional text window 20 are also provided for patient data and for entering appropriate diagnostic information. Multiple electronic images 42 may be displayed, as is shown in FIG. 2b.

Figure 3A:
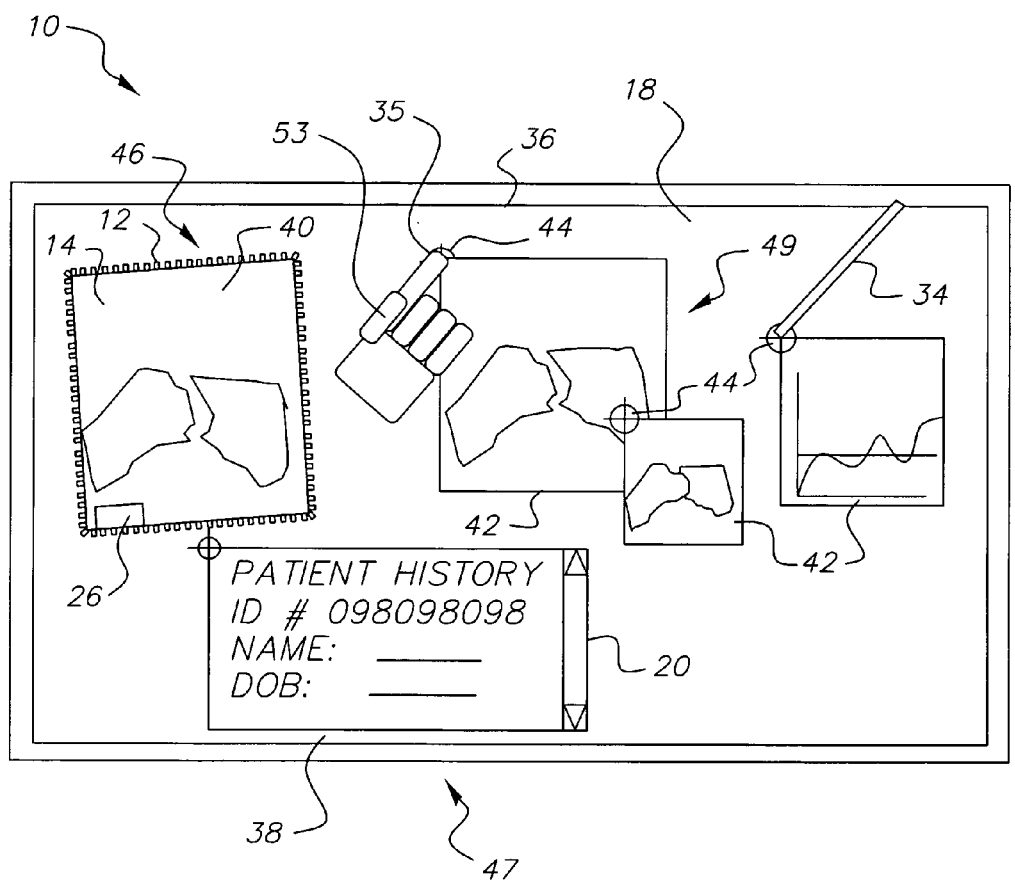
FIGS. 3a and 3b are plane views showing some of the user interface tools and options available with one embodiment of the viewing device of the present invention.

Referring now to FIG. 3a, various utilities are provided for manipulation of other illumination patterns such as a second illumination pattern 47 for text window 20 and a third illumination pattern 49 for electronic images 42. Electronic images 42 can be scaled and moved about display surface 38 using a conventional mouse interface device (not shown) or using touch-screen utilities. For example, a handle point 44 can be provided for each electronic image 42 or text area 20, enabling repositioning of electronic images 42. In the touch screen embodiment, a viewer can use a hand 53 to touch handle point 44 and simply drag its corresponding electronic image 42 to a more suitable location on display surface 38. Features such as scaling and overlapping are provided.

Zoom in, zoom out, re-centering, and scrolling functions are available for each displayed electronic image 42 or text window 20. Image rotation can also be varied as needed. These screen functions can be enabled by user interface system 30.

Figure 3B:
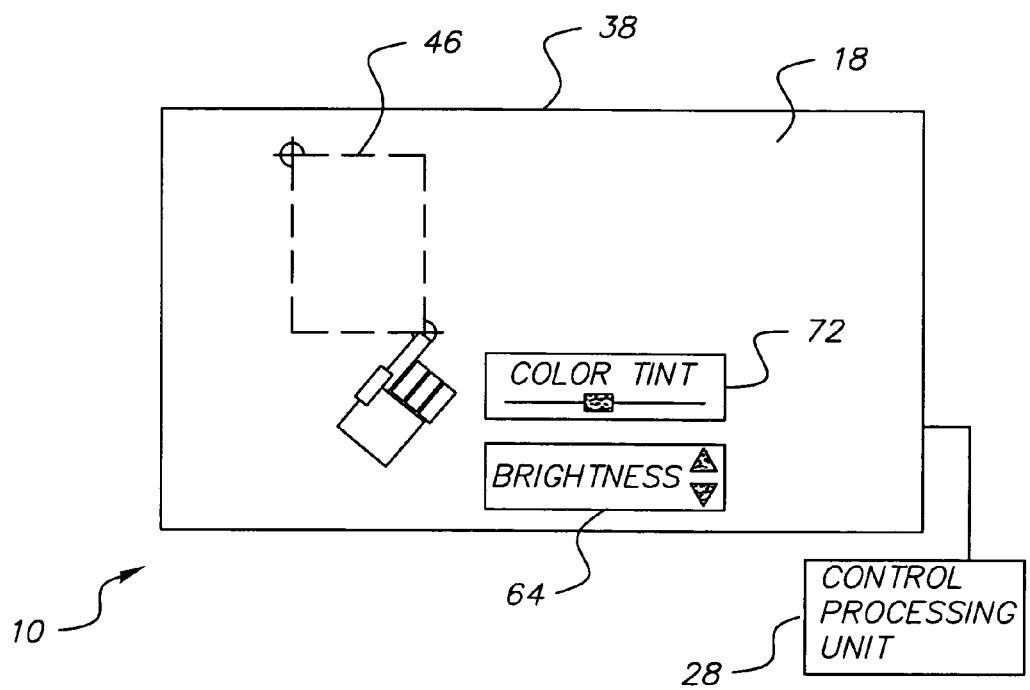

FIG. 3b shows one embodiment of a view of display 10 wherein control processing unit 28 obtains information from tracking memory 26 that indicates color or illumination characteristics of image-bearing film 40 or information from which color or illumination characteristics can be determined. Examples of such information include data indicating a type of image-bearing film 40, density characteristics of image-bearing film 40, an age of image-bearing film 40, and/or a density adjustment curve for image-bearing film 40. Control processing unit 28 causes the color, brightness, gamma and other characteristics of the backlight generated by illumination pattern 46 based upon the image information so that different images presented using display system 10 have a common appearance. As is shown in FIG. 3b, there are systems that allow for manually adjusting illumination pattern 46 as a backlighting area of display surface 38 that override such automatic controls. For example, brightness controls 64 are provided. Optionally, other color characteristics of illumination pattern 46 can be adjusted. In the embodiment on-screen interface color tint tools 72, such as the sliding bar shown in FIG. 3b, can be used, for example, to customize the color content of an image to suit the tastes of a particular viewer 48.

Image-bearing film 40 can be affixed to display surface 38 by means of conventional clips, such as those used with conventional X-ray backlight apparatus. Optionally, electrostatic attraction, magnetics, or vacuum force could be used to hold image-bearing film 40 in a position proximate to display surface 38 for viewing. Positional sensor 45 can cooperate with structures that provide such electrostatic attracting magnetics or vacuum force in order to locate the position and orientation of image-bearing film 40.

Sequence for Image Access

Patient privacy is one area of concern for allowing access to diagnostic images. Policies at a medical facility and/or legal requirements may dictate that only designated physicians and staff members have access to particular medical images and other patient information. In addition, there may be various levels of restriction enforced. For example, attending physicians for a patient may have unlimited access to the complete medical record, including all images and patient data. However, administrative staff members may be permitted access only to specific images and data relevant to a particular injury or treatment.

Figure 4:
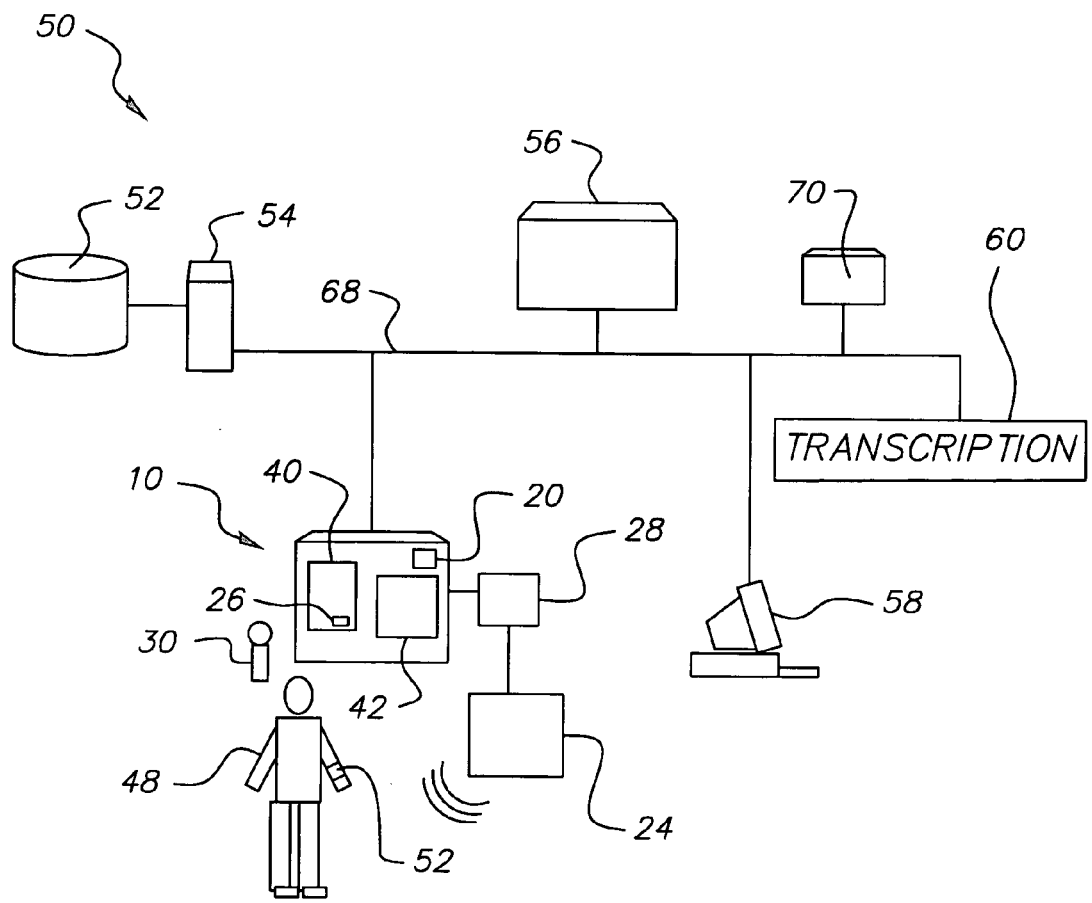
FIG. 4 is a schematic block diagram showing the use of a viewing device of the present invention as part of a larger networked medical diagnostic imaging system.

Referring to FIG. 4, viewing device 10 is shown as part of a larger diagnostic imaging and records maintenance system 50 on a network 68. In the embodiment of FIG. 4, diagnostic imaging and records maintenance system 50 includes a patient database 54, which contains one or both of patient data and medical images, one or more image capture systems 56, such as X-ray or ultrasound apparatus, an enhanced display apparatus 58 providing features such as stereoscopic and 3-D imaging, and a transcription service 60.

A viewer 48 can access data from viewing device 10 in a number of ways. In conventional networked systems, a login and password, entered on a keyboard, are required for access to image display. In the embodiment of FIG. 4, viewer 48 has a viewer identifier 52 that automates access security routines and, because viewer identifier 52 validates viewer 48 as having specific access permissions, minimizes or eliminates the need for login and password entry. Detection of viewer identifier 52 is similar to detection of image identifier 26 that is coupled to image-bearing film 40. In a preferred embodiment, as shown in FIGS. 1 and 4, RF transceiver 24 serves as the sensor for obtaining encoded information for both tracking memory 26 and viewer identifier 52.

Once control processing unit 28 validates the identity and access permissions of viewer 48 and obtains patient information from tracking memory 26, access is provided to various other subsystems of diagnostic imaging and records maintenance system 50. Information can be accessed from a patient database 54, including electronic images, patient history, billing data, and related information. An image capture system 56 may also be accessed, allowing updated electronic images 42 to be downloaded directly to viewing device 10. Image capture system 56 may be, for example, an X-ray or ultrasound imaging system. A stereoscopic/3-D display 58 may also be available as part of diagnostic imaging and records maintenance system 50, allowing an enhanced view of diagnostic images. Remote services, such as a transcription service 60, are also available to viewer 48 at viewing device 10.

Thus, as shown in FIG. 4, viewing device 10 serves as an access point for obtaining and updating patient data and image information across the complete diagnostic imaging and records maintenance system 50. An optional printer 70 enables viewer 48 to obtain a copy of one or more specific images or data for a patient.

User Interaction

As shown in the above description, viewing device 10 of FIG. 1 provides a platform for interaction with the overall diagnostic imaging and records maintenance system 50 of FIG. 4. There are a number of options for initiating and validating the use of viewing device 10. In the mode of access described hereinabove, viewer 48 positions image-bearing film 40 against viewing device 10 to initiate display operation. Sensing system 23, such as transceiver 24, obtains the necessary information from tracking memory 26 to identify the patient. Transceiver 24, or other sensor, then obtains the necessary information from viewer identifier 52 to identify viewer 48. Control processing unit 28 then validates viewer 48 permissions, in conjunction with control logic associated with patient database 54. Viewer 48, once authorized, is then permitted access to some or all of the patient images and data from patient database 54.

A number of variations is possible. For example, it may not be necessary to provide image-bearing film 40 in order to obtain access to patient images and other records. Tracking memory 26 can be embodied within a patient folder or on some other type of patient record that can be scanned by transceiver 24. Alternatively, viewer 48 may be presented with a listing of patients for whom viewer 48 has records access. This listing can be made available, for example, when viewer 48 is positioned within close proximity to viewing device 10. Viewer 48 can then select the patient or patients of interest from a listing and obtain records information.

As was noted earlier, different medical professionals may be allowed different levels of access to patient data. This means, for example, that some information might be excluded for read access from some viewers 48. This also allows various permissions to be granted for write access to patient data. For example, it may be desirable to deny write access for some or all parts of patient data to nursing staff, but allow write access to physicians.

Log Maintenance

One benefit of viewing device 10 as part of diagnostic imaging and records maintenance system 50 relates to the automated identification of viewer 48, whether or not manual login and password entry are used. This capability facilitates the maintenance of an electronic log that records information such as: what images were viewed at a particular time, and identity of viewer 48, the medical professional who accessed and viewed the images and patient data. The stored information also provides tracking data, including information on which medical professional has possession of a patient image or folder, for example.

Annotation

One benefit of the apparatus of the present invention relates to facility of annotation. Viewing device 10 provides a useful mechanism for recording various notes, instructions, and observations from members of the diagnosis and treatment staff. Annotation can be obtained in a number of different ways. Using user interface system 30, comments and annotation can be obtained while a medical professional is observing an image. Such comments and annotations can be obtained and converted into digital form using text based, video based, graphics based and or audio based embodiments of user interface system 30. The digital data obtained from such systems could be stored in patient database 54 or in some storage facility linked to patient database 54. Alternately, audio comments could be transcribed. Using transcription service 60, viewer 48 can simply make observations into audio capture system 33 and have text automatically stored in a file in patient database 54 and/or displayed on-screen in text window 20. Transcription service 60 could even be remotely located, using either human operators or speech recognition and text conversion software, for example. Transcribed text can then be displayed in text window 20, enabling editing and correction by viewer 48.

Similarly, written annotation can be obtained and recorded in a number of ways. As FIG. 1 showed, tablet 32 and stylus 34 provide one mechanism for annotation capture. Optionally, display surface 38 (FIG. 2a) could be a sensitive surface for accepting written annotation. This would enable recording of any handwritten text written on any part of display surface 38, including illumination pattern 46. The recorded annotations are then stored in association with the image transparency. This can be done by storing the annotation in a database that is electronically associated with recorded image 14, by storing the annotations in a patient oriented database and/or by storing the annotation in tracking memory 26.

System Interaction

It has been acknowledged that suitable ambient lighting conditions can be a factor in displaying diagnostic images effectively. For example, glare from overhead lighting can reduce the effective contrast in a displayed image, hindering accurate analysis and diagnosis. In one attempt to avoid unwanted light in the viewing environment, U.S. Pat. No. 6,595,922 entitled "Medical Diagnostic Ultrasound Imaging System with an Ambient Room Light" to Henderson et al. discloses an ultrasound imaging apparatus that is itself equipped with a light source that is optimized for operator viewing of the obtained image during the ultrasound session. Recognizing the importance of providing suitable ambient viewing conditions in addition to serving as a key user interface to diagnostic imaging and records maintenance system 50, viewing device 10 also acts as a mechanism for adapting the viewing environment to suit the preferences of individual viewers 48.

Figure 5:
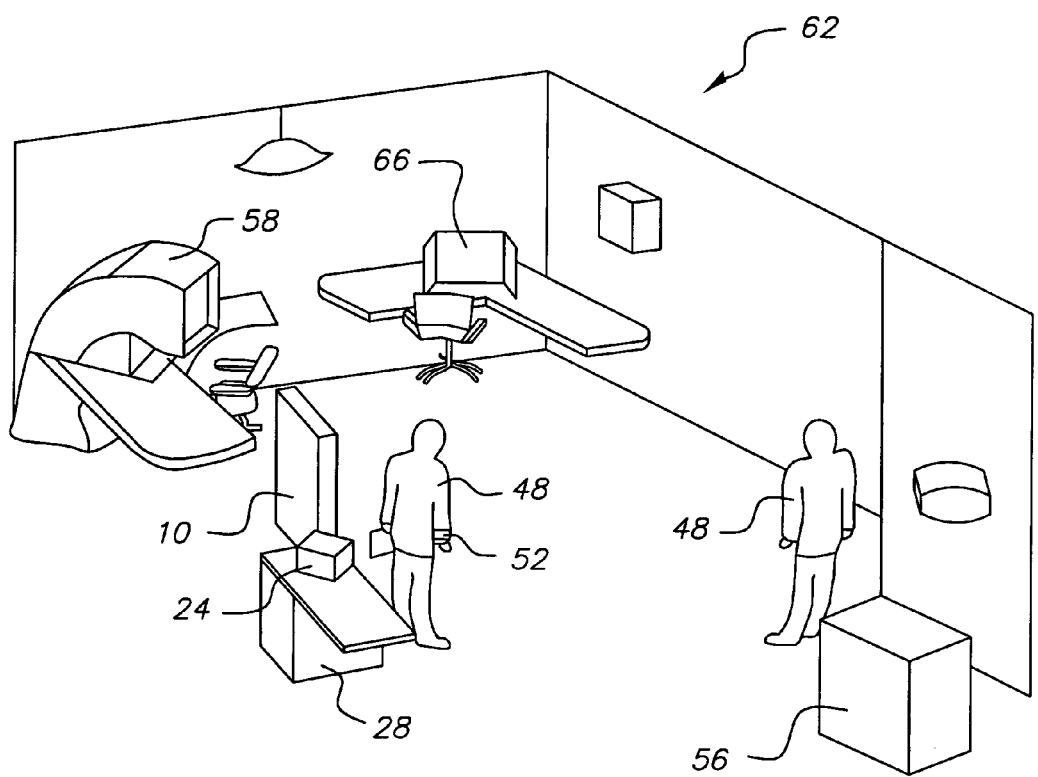
FIG. 5 is a block diagram showing a viewing area using one embodiment of viewing device according to the present invention.

Referring to FIG. 5, there is shown a viewing room 62 which provides an environment suited to viewing and assessment of diagnostic images. Viewing device 10, using transceiver 24 or other sensor, identifies viewer 48 in viewing room 62. Based on a known set of preferences for a specific viewer 48 or, by default, for the general preferences of the larger group of viewers 48, control processing unit 28 sets light intensity of both film and electronic image display areas of viewing device 10 and adjusts lighting conditions in viewing room 62 to an optimal level for viewing diagnostic images.

In addition to setting screen illumination and ambient light levels, control processing unit 28 may also adjust any number of other ambient conditions to the preferences of viewer 48. For example, it may be the preference of viewer 48 to adjust room temperature and humidity levels for preferred settings, particularly if viewer 48 intends to be working within viewing room 62 for an extended period of time. Other local preferences might include settings for background music, for example. Settings may be adjusted where there are multiple simultaneous viewers 48, such as providing additional levels of light with more than one viewer 48.

Viewing room 62 may optionally include stereoscopic/3-D display 58 and other display workstations 66. This arrangement, with multiple display apparatus available in the same viewing room 62, allows viewer 48 to select an image or images for viewing on viewing device 10, then to view images on stereoscopic/3-D display 58 for enhanced view capability, or on display workstation 66 for using diagnostic imaging software, for example. An optional printer 70 is also shown for rendering image bearing mediums.

As shown in FIG. 5, viewing room 62 may include a number of different display systems and may even include one or more image capture systems 56. Referring back to FIG. 4, connection of multiple apparatus on network 68 allows viewer 48 to work with an arrangement of diagnostic imaging systems and provides similar identification, logging, transcription, and records access capabilities at numerous points along network 68. Thus, for example, using the arrangement of viewing room 62, a physician can begin by viewing images on viewing device 10, then move to stereoscopic/3-D display 58 for a more detailed view, recording audible and written commentary while working at both of these imaging systems.

Advanced Capabilities

Using the preferred embodiment, the design of viewing device 10 also allows for a number of advanced capabilities that are well beyond what has been available using conventional light box displays. One substantial advantage of the use of a tracking memory 26 that comprises an radio frequency transponder relates to the capability for memory storage on the tracking memory itself. While initial versions of the RFID circuits provided only a relatively small amount of on-board memory, further development has created significant increases in memory capacity. Thus, there can be applications wherein a digital image that corresponds to an image recorded on an image-bearing film 40 can be stored in a memory of one or more radio frequency transponders that form a tracking memory 26 for image-bearing film 40. Using this capability, it can be possible to access at least some of a library of medical images directly from the tracking memory 26 for that patient. This capability may be useful, for example, where a limited number of images are needed for viewing, or where text, graphic icons or other annotations are to be stored in the memory of tracking memory 26.

The ability to write data to tracking memory 26 is another advantage of some but not all of the embodiments of the present invention. Unlike the barcode encoding described in the '516 Leiper disclosure, the memory in the radio frequency transponder type tracking memories can be modified. Thus, viewing device 10 can update memory circuitry on the radio frequency transponder components, including the capability to store alternate or updated images using such radio frequency transponders.

Another notable advantage of some but not all of the embodiments of the present invention relates to diagnostic imaging software. Using annotation tools, viewer 48 can isolate an area of image 14 for image analysis using diagnostic imaging software. In this way, working hand-in-hand with diagnostic analysis software, the apparatus and method of the present invention enable a broadened range of diagnostic capabilities for medical images.

Optional Embodiments

The present disclosure describes one embodiment using radio frequency transponders for tracking memory 26, viewer identifier 52 and wherein viewing device 10 comprises a sensing system 23 having a transceiver 24 rather than some other type of sensor. Other types of identifiers could alternately be used for one or both tracking memory 26 and viewer identifier 52. Other types of possible identifier/sensor components include magnetic strips, read from and recorded onto using a magnetic strip reader/writer, a conventional memory circuit or bar code markings where such alternate tracking memories 26 are used, appropriate co-designed sensing systems 23 will also be used.

Advantages of the radio frequency transponder embodiment of tracking memory 26 include proximity scanning, so that it is not necessary for viewer 14 to separately "swipe" the image encoding past a sensor, as is required with bar encoding and magnetic strips or to form an electrical connection as is required with conventional, non-RF enabled memory circuits.

The invention has been described in detail with particular reference to certain preferred embodiments thereof, but it will be understood that variations and modifications can be effected within the scope of the invention as described above, and as noted in the appended claims, by a person of ordinary skill in the art without departing from the scope of the invention.

PARTS LIST 10 viewing device
12 backlight portion
14 recorded image
15 digital image
16 electronic display portion
18 display screen
20 text window
22 keyboard console
23 sensing system
24 transceiver
26 tracking memory
27 RF transponder
28 control processing unit
30 user interface system
32 tablet
33 audio capture system
34 stylus
36 contact-sensitive surface
38 display surface
40 image-bearing film
42 electronic image
44 handle point
45 positional sensor
46 first illumination pattern
47 second illumination pattern
48 viewer
49 third illumination pattern
50 diagnostic imaging and records maintenance system
52 viewer identifier
53 hand
54 patient database
56 image capture system
58 stereoscopic/3-D display
60 transcription service
62 viewing room
64 brightness controls
66 display workstation
68 network
70 printer
72 color tint tools

What is claimed is:

1. A viewing device for simultaneously displaying an image transparency and at least one electronic image, comprising:
a display surface comprising:
an adjustable light-providing area for providing an area of backlight illumination through the image transparency;
an electronic image area for display of said at least one electronic image;
a transceiver for reading patient information from a radio frequency transponder coupled to the image transparency, said radio frequency transponder comprising a memory with patient information stored therein; and
a control processing unit, provided with a communication link for obtaining said at least one electronic image from a patient database using the patient information and causing the electronic image to be presented wherein the memory also stores information about light transmission characteristics of the image transparency and the control processing unit adjusts operation of the adjustable light-providing area based upon the light transmission characteristics.

2. The viewing device of claim 1, wherein said display comprises a light box portion having a light source and diffuser for providing the first illumination pattern and a dynamic display portion having a dynamically adjustable display for providing the second illumination pattern.

3. The viewing device of claim 1, further comprising a text entry surface to receive annotation information wherein the control processing unit stores the annotation information in association with the image.

4. The viewing device of claim 1, further comprising an audio capture system for recording audio information.

5. The viewing device of claim 1, wherein said display surface comprises a touch screen display surface.

6. The viewing device of claim 1, wherein said patient information includes a network address for obtaining said electronic image using the network.

7. The viewing device of claim 1, wherein said patient information includes at least one electronic image.

8. The viewing device of claim 1, wherein the memory stores patient identification information.

9. The viewing device of claim 1, wherein the memory also stores area of interest information and wherein the control processing unit adjusts operation of the adjustable light-providing area to illuminate the area of interest so that the light passing from the adjustable-light providing area through the area of interest has an appearance that is different from light passing from the adjustably light providing area through other areas of the transparency.

10. The viewing device of claim 1, wherein the transceiver further senses identifying data for radio frequency transponders associated with at least one person in a range proximate to the display, and the control processing unit determines permissions for viewing the image transparency based upon the identifying data and wherein the control processing unit causes the first illumination pattern to be formed only when at least one identified person has permission to view the image.

11. The viewing device of claim 1, further comprising an interface for communicating with other imaging devices wherein the control processing unit uses the obtained data to enable the other imaging devices to receive data related to the subject of the image transparency for presentation.

12. The viewing device of claim 1, wherein the transceiver further senses identifying data in radio frequency transponders that are associated with at least one person in a range proximate to the display and the control processing unit determines access permissions for each identified person and wherein the control processing unit uses the obtained data to enable other imaging devices only where at least one identified person has access privileges for viewing data related to the person.

13. The viewing device of claim 1, wherein the adjustable light providing area is capable of providing colored light and wherein the control processing unit sets the color of said backlighting window based upon information stored in the memory.

14. A display screen comprising:
- a backlighting window for providing backlight illumination through a transparency; and,
- a display window for displaying at least one electronic image;
- a radio frequency transceiver for obtaining data from a radio frequency transponder on the transparency, and
- a control processing unit that adjusts the appearance of at the backlighting window based upon data obtained from the radio frequency transponder, wherein said obtained data comprises at least one data that indicates a transparency type, transparency color characteristics, transparency age, and transparency density adjustment curve information.

15. The display screen of claim 14 wherein said obtained data includes patient identification data and the appearance of at least one window is determined based upon the patient identification data.

16. A method for operating a display for simultaneous viewing of an image transparency and at least one electronic image, comprising:
- detecting a tracking memory coupled to the image transparency;
- reading information from the tracking memory;
- forming a first illumination pattern for providing a backlighting source for an image transparency;
- forming a second illumination pattern for presenting an electronic image; and
- wherein at least one of the first illumination pattern and second illumination pattern are provided based upon the information read from the tracking memory and wherein the tracking memory also stores information about light transmission characteristics of the image transparency and the control processing unit adjusts the first illumination pattern based upon the light transmission characteristics.

17. The method of claim 16, further comprising the steps of identifying at least one viewer and determining permissions for viewing the illumination patterns based upon the permissions.

18. The method of claim 16, further comprising the steps of identifying at least one viewer and the step of setting ambient lighting conditions based upon user preferences for the identified viewer.

19. The method of claim 16, further comprising the steps of identifying at least one viewer and the step of setting ambient environmental conditions based upon user preferences for the identified viewer.

* * * * *